United States Patent [19]

Richter et al.

[11] 4,366,033

[45] Dec. 28, 1982

[54] METHOD FOR DETERMINING THE CONCENTRATION OF SUGAR USING AN ELECTROCATALYTIC SUGAR SENSOR

[75] Inventors: Gerhard Richter, Erlangen; Günter Luft, Lauf; Ulrich Gebhardt, Langensendelbach, all of Fed. Rep. of Germany

[73] Assignee: Siemens Aktiengesellschaft, Munich, Fed. Rep. of Germany

[21] Appl. No.: 29,128

[22] Filed: Apr. 11, 1979

[30] Foreign Application Priority Data

Apr. 20, 1978 [DE] Fed. Rep. of Germany ....... 2817363

[51] Int. Cl.³ ............................................. G01N 27/52
[52] U.S. Cl. ..................................... 204/1 T; 128/635; 204/195 B; 204/195 P
[58] Field of Search ................... 204/1 P, 1 E, 195 P, 204/195 B, 1 T; 128/635

[56] References Cited

U.S. PATENT DOCUMENTS

| | | | |
|---|---|---|---|
| 3,305,468 | 2/1967 | Liesch | 204/195 T |
| 3,539,455 | 11/1970 | Clark | 204/1 E |
| 3,551,109 | 12/1970 | Dahms | 204/195 T |
| 3,770,607 | 11/1973 | Williams | 204/195 P |
| 3,837,339 | 9/1974 | Aisenberg et al. | 128/213 |
| 3,979,274 | 9/1976 | Newman | 204/195 P |

FOREIGN PATENT DOCUMENTS 1422172 1/1976 United Kingdom .

OTHER PUBLICATIONS

Gebhardt, U. et al., Biomed Technik, 22, pp. 399 and 400, (1977).
Kuo Wei Chang et al., Amer. Soc. Artif. Int. Organs, vol. 19, pp. 352-360, (1973).

*Primary Examiner*—G. L. Kaplan
*Attorney, Agent, or Firm*—Kenyon & Kenyon

[57] ABSTRACT

A method for determining the concentration of sugar in the presence of interfering foreign substances, particularly for determining glucose in a body fluid, by means of an electrocatalytic sugar sensor which has a measuring electrode in which the measuring electrode is alternatingly set potentiostatically to a reactivation and a measuring potential and the current flowing during the measuring period is evaluated as the measurement signal. To prevent foreign substances from exerting an interfering influence and thereby permit a sensitive sugar determination which is reliable over an extended period of time, a hydrophilic diaphragm is arranged in front of the measuring electrode to impede the resupply of the interfering foreign substances to the measuring electrode so that a diffusion limit current adjusts itself during the reactivation phase in the oxidation of the foreign substances; and the current is evaluated with a time delay relative to the start of the measuring period.

13 Claims, 5 Drawing Figures

METHOD FOR DETERMINING THE CONCENTRATION OF SUGAR USING AN ELECTROCATALYTIC SUGAR SENSOR

BACKGROUND OF THE INVENTION

This invention relates to the determination of the concentration of sugar in the presence of interfering foreign substances, especially determination of glucose in a body fluid, in general, and more particularly to a method using an electrocatalytic sugar sensor comprising a measuring electrode, wherein the potential of the measuring electrode is alternatingly set to a reactivation and a measuring potential and the current flowing during the measuring period is evaluated as the measurement signal, as well as to an electrocatalytic sugar sensor for implementing this method.

The determination of the sugar concentration in a body fluid, especially the blood of a patient, is important, for instance, in the case of diabetics, since it is important for a diabetic that the normal blood glucose level be kept constant through the day. The blood glucose level can be influenced by the diet, by insulin injections and by motion therapy. It is essential in this connection that over or under compensation of the sugar content of the blood be avoided. For the patient himself it is important to know the prevailing blood sugar content, so that he can take suitable measures for controlling it if necessary.

Regulation of the glucose concentration automatically by means of a so-called artificial beta-cell has also been considered by controlling the insulin supply to the blood via a glucose sensor wherein insulin is always supplied to the blood, if desired, proportionally to a glucose reference value, when the glucose reference value is exceeded.

Heretofore, the glucose in the blood has generally been determined externally in a clinical laboratory by photometric means. However, electrochemical sensors are also known which make it possible to determine the glucose in the body fluid. In a so-called enzyme sensor, the glucose is oxidized to gluconic acid by means of glucose oxidase, wherein oxygen is consumed and hydrogen peroxide is formed. The oxygen consumption and the formation of hydrogen peroxide can be measured electrochemically, and a signal is thus obtained which is related to the glucose concentration. Since the enzyme sensor operates selectively and does not respond to foreign substances, it is possible to make a reproducible glucose determination, but it is not suitable for long term implantation because the enzymes, like all other proteins, decay under physiological conditions in the course of time; i.e., they are not stable over the long term under body conditions.

An electrocatalytic glucose sensor is known, for instance, from British patent specification No. 1,422,172. However, this sensor also is not stable over the long term if it is operated with potential control. With current controlled operation, on the other hand, the sensitivity is lower than desired.

While intermittent measurements have been possible heretofore with electrocatalytic glucose sensors, especially relative measurements (see in this connection: "Trans. Amer. Soc. Artif. Int. Organs", vol. XIX, 1973, pages 352 to 360) interference with the measurement signal still always takes place due to coreactants. For, impurities and accompanying substances can then either be oxidized at the measuring electrode and thereby falsify the measurement signal, or can limit the activity of the measuring electrode due to blocking. In the case of implantable sensors, furthermore, components of the body fluid, especially urea and amino acids, have been found to have an interfering effect, as they thwart a reproducible long-term measurement.

This applies in essence also to an implantable electrocatalytic glucose sensor which is described in the journal "Biomed. Technik", 22 (1977), pages 399 and 400. This sensor, which comprises a measuring electrode, counter electrode and reference electrode, is operated in accordance with the so-called voltage-jump method, i.e., a measuring and a reactivation potential are impressed alternatingly on the measuring electrode. During the measuring time, the current is integrated and at the end of the measuring time, this integral represents the measurement value.

SUMMARY OF THE INVENTION

It is an object of the present invention to develop a method for determining the concentration of sugar of the kind mentioned at the outset in which a reactivation and a measuring potential are alternatingly impressed on the measuring electrode and the current flowing during the measuring period is evaluated as the measurement signal, in such a way that a sugar determination which is sensitive and reliable over a long period of time is possible, even in body fluids.

According to the present invention, this is achieved by the provision that, through a diaphragm in front of the measuring electrode, the supply of the interfering foreign substances to the measuring electrode is impeded to such an extent that, in the reactivation phase, a diffusion limit current appears during the oxidation of the foreign substances, and that the evaluation of the current is made with a time delay relative to the start of the measuring period.

By means of the method according to the present invention, it is possible to make a reproducible long term measurement of the sugar content even in heavily "contaminated" liquids such as, for instance, body fluids, as the interference caused by foreign substances is eliminated.

The foreign and interference substances present in body fluids are generally more difficult to oxidize than glucose; easily oxidized substances such as cystein, occur only in very low concentrations. In principle, it would therefore be possible to determine glucose under mild oxidation conditions, if no blocking of the catalyst surface took place due to other, firmly adhering accompanying substances. With the method according to the present invention, it is possible to eliminate this blocking by oxidizing, on the one hand, the measuring electrode at a strongly anodic potential, i.e., at a potential above 800 mV (measured against the reversible hydrogen electrode), and on the other hand, at the same time placing a tight diaphragm which inhibits a resupply of the substances having a blocking effect in front of the measuring electrode. Since, with such a procedure, the electrode surface is continuously cleaned by anodic oxidation of the blocking adsorption products (reactivation phase), long term operation can be guaranteed with the method according to the present invention. At the same time, a diffusion limitation of the glucose is ensured, so that the measurement signal is independent of the activity of the measuring electrode.

In the method according to the present invention, the measurement itself then takes place, after a potential jump, at a lower potential, for instance, at 400 mV, i.e., at a potential at which most amino acids are not oxidized, so that no appreciable disturbance of the glucose measurement signal occurs. If, on the other hand, the measurement were to take place at the strongly anodic potential of the reactivation phase, then a faulty measurement result would always be obtained, because of the simultaneous oxidation of glucose and the accompanying substances, if the concentration of the accompanying substance varies. Therefore, the measuring potential is separated from the reactivation potential. In order to obtain high sensitivity in the sugar determination, the measurement signal, in addition, is not evaluated starting immediately when the potential is switched, but only after a delay, i.e., at a time when the large capacitive currents which do not depend on the sugar concentration, have decayed.

In the method according to the present invention, the reaction charge is preferably determined, i.e., the current flowing during the measurement period is integrated (with the corresponding time delay). The integration is advantageously started after a delay of up to 10 sec. and preferably, after 2 sec. The measurement itself is advantageously performed at a potential between 100 and 800 mV, referred to a reversible hydrogen electrode in the same solution. Since the potential is chosen so that, while oxidation of the glucose takes place, oxidation of the accompanying interfering substances does not, the measurement is preferably carried out at a potential of about 400 mV. The measurement is preferably carried out in a time of less than 1 min. Advantageously, the measuring period and the reactivation phase are chosen of equal length.

In order to obtain complete reactivation of the measuring electrode it is necessary to adapt the permeability of the diaphragm in front of the measuring electrode to the activity and the potential of the electrode in such a manner that the latter is in a condition to completely oxidize all arriving interfering substances during the reactivation potential. This means that a diffusion limit current is set with respect to the interfering substances.

It does not make sense to increase the activity of the electrode beyond a certain measure, since greater activity brings about a greater thickness of the active layer and therewith causes a time delay, and, in addition, enters strongly into the energy consumption of the system. It is also not possible to increase the electrode potential arbitrarily because oxygen starts to develop above a certain potential and the sugar sensor becomes useless as soon as gas collects between the electrode and the diaphragm. In the method according to the present invention, the reactivation is therefore performed advantageously at a potential of more than 800 mV; the reactivation potential is preferentially $\geq 1500$ mV. The permissible value also depends on the duration of the reactivation. Thus, gas development still does not take place even at 1600 mV within a period of about 25 sec, a period in which the measurement as well as the reactivation are carried out preferentially.

In an electrocatalytic sugar sensor for carrying out the method according to the present invention, which comprises a measuring electrode, a counter electrode and a reference electrode, a hydrophilic diaphragm is arranged in front of the active surface of the measuring electrode. The permeability and the thickness of the diaphragm in front depend on the desired diffusion limitation of the measurement signal and on the desired measuring time. The time constant of the sugar sensor depends on these variables: It is determined by $T = 0.167 \, d^2/D$; d being the thickness of the diaphragm and D the diffusion coefficient. In order to ensure the diffusion limitation, a diffusion coefficient as small as possible is desired, i.e., a diffusion coefficient smaller than $10^{-7}$ cm$^2$ sec$^{-1}$, where the lower limit is predetermined by the technical data of the current measurement. At the same time, in order to ensure the required time constant (it should be less than 10 min), the diaphragm should be less than 100 um thick.

To prepare diaphragms of such low permeability as has been set forth above, one can advantageously start out with plastics such as polyethylene and silicone, which form relatively hydrophobic foils and have been made hydrophilic by suitable measures, especially radiation grafting with acrylic acid, methacrylic acid or chlorosulfonic acid, i.e., by radiation chemical graft polymerization. The diaphragm used in the electrocatalytic glucose sensor according to the present invention preferably consists of hydrophilized polytetrafluoro ethylene.

The diaphragm can be arranged in front of the active surface of the measuring electrode in such a manner that the latter is covered with a prefabricated diaphragm. However, since such a procedure is technically disadvantageous, the diaphragm is advantageously prepared directly on the active surface of the measuring electrode, and specifically, from a solution. This procedure can be used particularly if a hydrophobic polymer is dissolved in a solvent together with a hydrophilic, water-insoluble polymer and is applied to the electrode surface by an immersion method. Through evaporation of the solvent, the solution dries up and a well-adhering foil is formed on the electrode surface. In a treatment with water or physiological solution, the diaphragm is later made to swell up again, if necessary by boiling. The hydrophobic polymer is advantageously contained in excess in the solution used for the preparation of the diaphragm. A sufficiently impermeable film is obtained if the content of the hydrophilic polymer in the polymer solution is less than 25% and preferably less than 10%. As the hydrophilic polymer, primarily sulfonated polytetrafluoroethylene is suitable, which, with a equivalent weight of less than 1000, is soluble in ethanol, isopropanol water mixtures and dimethylformamide. Polyacrylnitril and especially polyvinylidene fluoride are suitable as the hydrophobic polymer.

The electrocatalytic sugar sensor according to the present invention is advantageously constructed as a single rod measuring chain, the measuring electrode, counter electrode and reference electrode being integrated in one unit. The measuring electrode and the counter electrode and preferably arranged one behind the other, only one of the electrodes being adjacent to the body fluid. This electrode, facing the body fluid, is porous and is covered, toward the body fluid, by a hydrophilic diaphragm, while the other of the two electrodes is arranged in a closed space. In this manner it is ensured that the current can advance to the second electrode.

The active layer of the measuring electrode can consist of a noble metal catalyst layer; preferably, it consists of an activated platinum-iron metal alloy. The catalytic layer, which optionally can be doped with metallic additions, is preferably arranged on a metallic support structure (cf. German Pat. No. 24 05 475). The alloy film can be produced on the support structure advantageously by vapor deposition or by sputtering, i.e., removal of metals by electron bombardment, and subsequent precipitation. The alloy layer is activated, i.e., the inactive iron metal component is dissolved out, preferably by potentiostatic dissolution in sulfuric acid.

The counter electrode of the sugar sensor according to the present invention can advantageously serve at the same time as the reference electrode and consist, to this end, for instance, of silver chloride. However, the functions of the counter electrode and the reference electrode are preferably separated and the counter electrode is constructed as a selective oxygen electrode. Then the counter electrode is advantageously arranged in front of the measuring electrode, is made porous and thin and consists of carbon or silver; the thickness of the counter electrode is then advantageously less than 100 um and preferably less than 20 um.

DETAILED DESCRIPTION OF THE INVENTION

Figure 1:
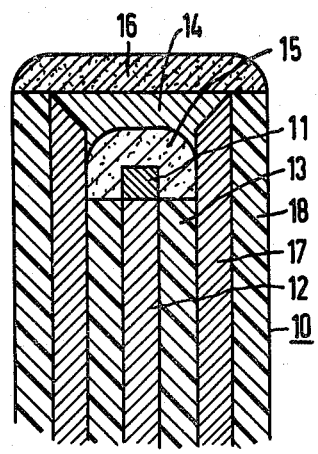
FIG. 1 is a cross section through a first embodiment of the electrocatalytic sugar sensor of the present invention.

In FIG. 1, a cross section through a rotationally symmetrical embodiment of the electrocatalytic sugar sensor according to the present invention is shown. In this embodiment the counter electrode also serves as the reference electrode. The sugar sensor 10 contains, for this purpose, a counter electrode 11 in the form of a consumable silver chloride electrode. Since the silver chloride electrode 11 has a constant potential, it can serve at the same time as the reference electrode. The current lead 12 to the counter electrode 11 has an insulating jacket 13. The measuring electrode 14 of the sugar sensor 10 is separated from the counter electrode or reference electrode 11 by a hydrophilic diaphragm 15, which fills the space between the measuring electrode and the counter electrode. The measuring electrode 14, which is porous, is covered by a hydrophilic diaphragm 16 of low permeability. The measuring electrode 14 can consist, for instance, of sintered platinum powder. However, a measuring electrode with an active layer of Raney platinum which was prepared by dissolving nickel from a layer of platinum-nickel alloy vapor deposited on a substrate material can also be used. The sleeve-like lead 17 to the measuring electrode 14 is covered toward the outside by an insulating jacket 18. The insulating jacket 18 can consist, like the insulating jacket 13 between the leads 12 and 17, of an insulating plastic or varnish.

During the operation of the electrocatalytic sugar sensor, pH-shifts occur at the measuring electrode and the counter electrode in the course of the reaction. These pH-shifts can lead, in the case of an implanted sensor, to damage to the surrounding tissue. The tissue cannot stand a deviation of the pH-value very well, particularly in the alkaline direction. So that the pH-shifts are made ineffective toward the outside, the measuring electrode and the counter electrode are therefore arranged, as shown in FIG. 1, one behind the other in a unit. Here, the pH-shifts are equalized in the space between the measuring electrode 14 and the counter electrode 11, so that, during steady state operation, no appreciable deviation from the neutral value toward the outside takes place. The diaphragm 15 which is arranged in the space between the electrodes 11 and 14, can furthermore advantageously consist of ion exchanger material.

Figure 2:
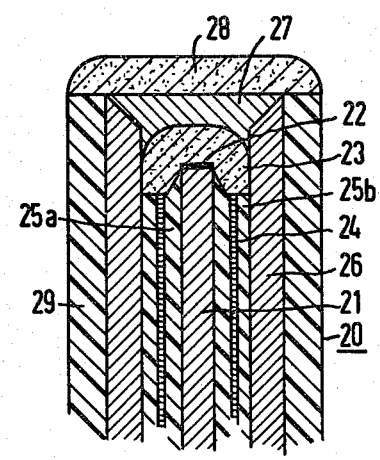
FIG. 2 is a similar view of a second embodiment of the present invention in which the functions of the counter electrode and reference electrode are separated.

In FIG. 2 an embodiment of the sugar sensor according to the present invention, in which the functions of the counter electrode and the reference electrode are separated is shown in a cross section. The measuring electrode 21 of the sugar sensor 20 in this embodiment has the form of a platinum wire which is provided with an active layer 22 of platinum black. The active surface of the measuring electrode, i.e., the layer 22, is surrounded by a tight diaphragm 23. The measuring electrode 21 is surrounded by a tubular reference electrode 24 of silver, which is in contact with the diaphragm 23. At the point of contact, the silver is chlorinated, i.e., changed to silver chloride. The Ag/AgCl reference electrode 24 is separated by an insulating layer 25a from the measuring electrode 21 and by an insulating layer 25b from the lead 26 for the counter electrode 27. The counter electrode 27, which adjoins the diaphragm 23, is a porous selective oxygen electrode and consists preferably of silver or carbon. Due to the fact that such a counterelectrode is not consumed, the life of the sugar sensor is not limited. The counter electrode 27 can be prepared, for instance, from a vapor deposited silver alloy by oxidizing dissolution of the less noble component, i.e., by the Raney process, or from a silver compound by reduction, and be provided with pores by the photoresist method. The counter electrode 27 is covered up toward the outside, i.e., toward the body fluid or the tissue, by a body-compatible, hydrophilic, thin, permeable diaphragm 28, through which oxygen and glucose can diffuse. The lead 26 to the counterelectrode 27, finally, is provided with an insulating jacket 29.

As an alternative to platinum black, the active layer 22 of the measuring electrode 21 may also consist of an active platinum metal which was made from an iron metal-platinum metal alloy. The alloy layer can be produced by vapor deposition or sputtering and may optionally be doped with tantalum or tungsten. The active Raney catalyst layer can be formed by potentiostatic dissolution of the iron metal in sulfuric acid.

Figure 3:
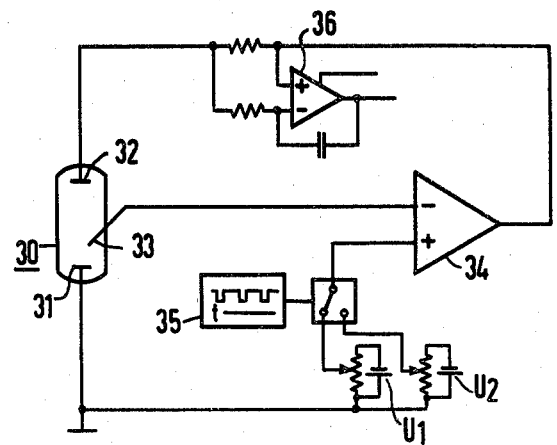
FIG. 3 is a circuit diagram of a measuring arrangement for use with the present invention.

In FIG. 3, the basic design of the measuring arrangement used in the method according to the invention is shown. The measuring cell 30, i.e., the sugar sensor proper, contains a measuring electrode 31, a counter electrode 32 and a reference electrode 33. The potential of the measuring electrode 31 is controlled by a potentiostat 34 by means of a program timer 35 in such a way that alternatively, a desired potential $U_1$ is set as the measuring potential and a desired potential $U_2$ as the reactivation potential. The current then flowing is evaluated by means of an integrator 36 to obtain the measurement signal.

As already mentioned, the evaluation of the measurement signal does not start immediately after the measuring potential is switched on, but only after a time delay. For, the charge of the double-layer capacity is first reversed and the oxidized surface layer of the platinum electrode reduced. The current then flowing has no relation to the glucose concentration. Therefore, a considerable increase in the sensitivity is obtained if the evaluation of the glucose oxidation current is started only after the initial, large capacitive current has decayed.

EXAMPLE 1

A platinized platinum electrode with an active area of 0.03 cm² is polarized alternatingly to 400 and 600 mV, a silver/silver chloride electrode serving as the reference electrode. The counter electrode, which likewise consists of platinized platinum is separated from the measuring electrode by a diaphragm. The platinizing is performed from a 2.5% solution of hexachloroplatinic acid at a current density of 30 mA/cm² for a period of 5 minutes. Thyrode solution is used as electrolyte, which consists of 125 mMol sodium chloride, 2.68 mMol potassium chloride, 1.8 mMol calcium chloride, 1.05 mMol magnesium chloride, 0.417 mMol sodium dihydrogen phosphate and 12 mMol sodium hydrogen carbonate. In order to keep the partial oxygen pressure and the pH value of the solution constant during the test, flushing with a mixture of 95% air and 5% carbon dioxide is applied.

Figure 4:
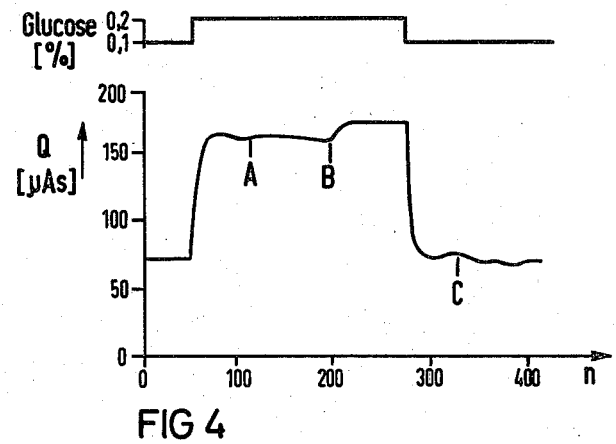
FIGS. 4 and 5 are curves helpful in understanding the operation of the present invention.

In FIG. 4, the course of the measurement signal is shown as a function of the number of measuring periods if the glucose and amino acid concentration in the solution is changed. In the upper part of the figure, the glucose concentration is shown. From the shape of the measurement signal it is seen that while it depends clearly on the glucose concentration, it responds only little to a change of the amino acid content, which took place at A (smallest occurring physiological amino acid concentration), B (highest occurring physiological amino acid concentration) and C (one-half of the highest occurring physiological amino acid concentration). Upon a change of the amino acid concentration from a mean value to 0 or to a maximum value, a deviation of the measurement signal of only a maximum of 5% is observed. In the present case, the measurement signal was 400 mV and the reactivation potential 1600 mV; the measuring and the reactivation time were of equal length and were 25 sec each. The diaphragm in front of the measuring electrode was a diaphragm of polytetrafluoroethylene with sulfonic acid groups coupled-on by radiation grafting.

Figure 5:
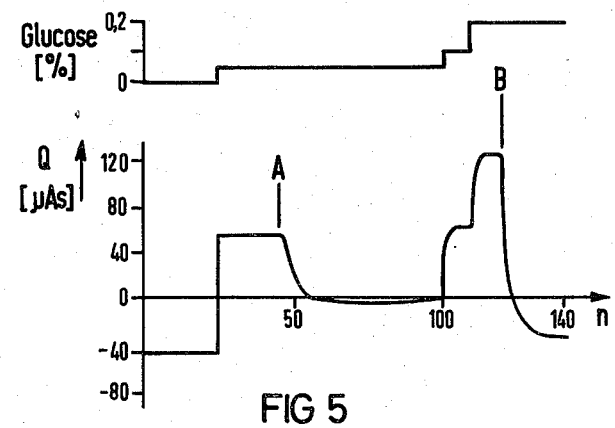

If the above-described test is made with a sugar sensor, in which a diaphragm of cellulose acetate is used instead of the diaphragm mentioned, a stronger influence of the amino acid concentration of the solution is noted. As shown in FIG. 5, the measurement signal responds to a change in the amino acid concentration (at A and B) with a change of the same order of magnitude as occurs for normal glucose concentration fluctuations.

The influence of the amino acid shows up even more, if the same test is made without a diaphragm in front. Also where the reactivation potential in the present case is fixed at 1200 mV, a strong amino acid influence is found. If the integration is performed immediately from the start of the measuring period on, i.e., without inserting a time delay, then no dependence on the glucose concentration is found at all.

EXAMPLE 2

A platinized platinum electrode corresponding to Example 1 with an electrode area of 0.03 cm² is coated by immersion in a solution of 6 g of sulfonated polytetrafluoroethylene prepared by copolymerization with an equivalent weight of 950, and 24 g polyvinylidenefluoride in 100 ml dimethyl formamide with a film which is fixed on the electrode surface by drying and absorbs water again by boiling and thereby becomes permeable for glucose. The thickness of the diaphragm prepared in this manner is about 50 μm and the diffusion coefficient of the glucose in this diaphragm is about $3 \times 10^{-8}$ cm² sec$^{-1}$. A sugar sensor containing such a measuring electrode provides a measuring error of less than 5% if the amino acid concentration in a glucose solution is changed from 0 to the maximum physiological value.

What is claimed is:

1. A method for determining the concentration of sugar in the presence of interfering foreign substances, especially for determining glucose in a body fluid, by means of an electrocatalytic sugar sensor comprising a measuring electrode, the measuring electrode adapted to be alternatingly set potentiostatically to a reactivation potential and a measuring potential and the current flowing during the measuring period evaluated as the measurement signal, comprising impeding the resupply of the interfering substances to the measuring electrode by a hydrophilic diaphragm, of a thickness less than one hundred micrometers and a diffusion coefficient for glucose of less than $10^{-7}$ cm² sec$^{-1}$, placed in front of the measuring electrode in such a manner that a diffusion limit current adjusts itself during the reactivation phase in the oxidation of the foreign substances, and performing the evaluation of the current after a time delay relative to the start of the measuring period.

2. The method according to claim 1, wherein the reaction charge is determined as the measurement signal by integrating the current in the measuring period.

3. The method according to claim 2, wherein the integration of the current is started after a delay of up to 10 sec.

4. The method according to claim 2 wherein, integration of current is started after a delay of about 2 seconds.

5. The method according to claim 1 wherein the measurement is made at a potential between 100 and 800 mV, relative to the potential of a reversible hydrogen electrode.

6. The method according to claim 5 wherein said measurement is made at a potential of about 400 mV, relative to the potential of a reversible hydrogen electrode.

7. The method according to claim 1, wherein the reactivation is performed at a potential above 800 mV, relative to the potential of a reversible hydrogen electrode.

8. The method according to claim 7 wherein said reactivation is performed at a potential equal to or above 1500 mV, relative to the potential of a reversible hydrogen electrode.

9. The method according to claim 1 wherein the measurement is made in a time of less than 1 min.

10. The method according claim 1 wherein the measuring period and the reactivation phase are chosen to be of about the same length.

11. The method according to claim 10, wherein the measurement and the reactivation are each executed in a time of about 25 sec.

12. The method according to claim 1 wherein, said hydrophilic diaphragm consists of hydrophilized polytetrafluoroethylene.

13. The method according to claim 1 wherein, said measuring electrode has an active layer which consists of activated platinum metal-iron metal alloy.

* * * * *